(12) United States Patent
Bartsch et al.

(10) Patent No.: US 7,528,275 B2
(45) Date of Patent: May 5, 2009

(54) METHOD FOR THE PRODUCTION OF ADIPODINITRILE BY HYDROCYANATION OF 1,3-BUTADIENE

(75) Inventors: Michael Bartsch, Neustadt (DE);
Robert Baumann, Mannheim (DE);
Gerd Haderlein, Grünstadt (DE);
Miguel Angel Flores, Aranjuez (ES);
Tim Jungkamp, Kapellen (BE);
Hermann Luyken, Ludwigshafen (DE);
Jens Scheidel, Hirschberg (DE);
Wolfgang Siegel, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 470 days.

(21) Appl. No.: 10/586,450

(22) PCT Filed: Jan. 26, 2005

(86) PCT No.: PCT/EP2005/000717

§ 371 (c)(1),
(2), (4) Date: Jul. 18, 2006

(87) PCT Pub. No.: WO2005/073167

PCT Pub. Date: Aug. 11, 2005

(65) Prior Publication Data

US 2008/0221351 A1    Sep. 11, 2008

(30) Foreign Application Priority Data

Jan. 29, 2004    (DE) .................. 10 2004 004 682

(51) Int. Cl.
*C07C 253/08*    (2006.01)
(52) U.S. Cl. ...................................... 558/332
(58) Field of Classification Search ............... None
See application file for complete search history.

(56) References Cited

U.S. PATENT DOCUMENTS

| 3,496,215 A | 2/1970 | Drinkard et al. |
| 3,850,973 A | 11/1974 | Seidel et al. |
| 6,169,198 B1 | 1/2001 | Fischer et al. |
| 6,242,633 B1 | 6/2001 | Fischer et al. |
| 2001/0014647 A1 | 8/2001 | Fischer et al. |
| 2004/0063956 A1 | 4/2004 | Burattin et al. |
| 2004/0063991 A1 | 4/2004 | Burattin et al. |
| 2004/0176622 A1 | 9/2004 | Bartsch et al. |

FOREIGN PATENT DOCUMENTS

| DE | 10046025 A1 | 3/2002 |
| FR | 2830530 A1 | 4/2003 |
| WO | WO-0230854 A2 | 4/2002 |
| WO | WO-0230854 A3 | 4/2002 |
| WO | WO-02/053527 A1 | 7/2002 |
| WO | WO-03011457 A1 | 2/2003 |

OTHER PUBLICATIONS

J. Montgomery; Science of Synthesis; 2001; Georg-Thieme Verlag, Stuttgart; p. 11 to p. 62.
W.C. Seidel and C.A. Tolman; Annals of the New York Academie of Sciences; vol. 415, 1983; p. 201 to 211.
C.A. Tolman et al; "Catalytic Hydrocyanation of Olefins by Nickel (O) Phosphite Complexes—Effects of Lewis Acids" in Organometallics, vol. 3; 1984; p. 33 to 38.

*Primary Examiner*—Kamal A Saeed
(74) *Attorney, Agent, or Firm*—Connolly Bove Lodge & Hutz LLP (57) ABSTRACT

A process is described for preparing adiponitrile by hydrocyanating 1,3-butadiene over a catalyst, by, in a first process step, hydrocyanating 1,3-butadiene to 3-pentenenitrile over at least one nickel(0) catalyst, and, in a second process step, hydrocyanating 3-pentenenitrile to adiponitrile over at least one nickel(0) catalyst with addition of at least one Lewis acid, wherein at least one of the at least one nickel(0) catalysts used in the particular process steps is transferred into the other process step.

16 Claims, 2 Drawing Sheets

METHOD FOR THE PRODUCTION OF ADIPODINITRILE BY HYDROCYANATION OF 1,3-BUTADIENE

CROSS REFERENCE TO RELATED APPLICATIONS

This application is a National Phase of PCT/EP2005/0007 17, filed January 26, 2005, which claims priority to German application 10 2004 004 682.4.

The present invention relates to a process for preparing adiponitrile by hydrocyanating 1,3-butadiene over a catalyst.

Adiponitrile is an important starting material in nylon production which is obtained by double hydrocyanation of 1,3-butadiene. In a first hydrocyanation, 1,3-butadiene is hydrocyanated to 3-pentenenitrile, and the by-products obtained are mainly 2-methyl-3-butenenitrile, 2-pentenenitrile, Cg nitriles and methylglutaronitrile. In a second, subsequent hydrocyanation, 3-pentenenitrile is reacted with hydrogen cyanide to give adiponitrile. Both hydrocyanations are catalyzed by nickel(0) phosphorus complexes. In addition, a Lewis acid, for example $ZnCl_2$, $FeCl_2$, $Et_2AlCl$, $Et_3Al_2Cl_3$ or $EtAlC_2$, is added in the second hydrocyanation of 3-pentenenitrile.

The existing processes for preparing adiponitrile recycle the catalysts used in the individual hydrocyanations generally into the particular hydrocyanations. However, the existing processes for preparing adiponitrile by hydrocyanating 1,3-butadiene and subsequently hydrocyanating the resulting 3-pentenenitrile do not exhibit any connection of the catalyst circuits used in the two hydrocyanations. For process economics reasons, this is, though, advantageous.

It is accordingly an object of the present invention to provide an integrated process for preparing adiponitrile by double hydrocyanation of 1,3-butadiene, which enables connection of the catalyst circuits of the two hydrocyanations during the preparation of adiponitrile.

The achievement of this object starts from a process for preparing adiponitrile by hydrocyanating 1,3-butadiene over a catalyst, by in a first process step, hydrocyanating 1,3-butadiene to 3-pentenenitrile over at least one nickel(0) catalyst and in a second process step, hydrocyanating 3-pentenenitrile to adiponitrile over at least one nickel(0) catalyst with addition of at least one Lewis acid.

The process according to the invention comprises transferring, at least one of the nickel(0) catalysts used in the particular process steps at least partly to the other process step.

The connection of the above-described catalyst streams makes possible an economically viable process for preparing adiponitrile.

In a particularly preferred embodiment of the present invention, the process according to the invention is characterized by the following process steps:

(a) hydrocyanating 1,3-butadiene over at least one nickel(0) complex as a catalyst, resulting in a hydrocyanation stream 1 which comprises 3-pentenenitrile, 2-pentenenitrile, 2-methyl-2-butenenitrile, $C_9$ nitrites, 2-methyl-3-butenenitrile, the at least one nickel(0) catalyst, methylglutaronitrile, unconverted 1,3-butadiene and residues of unconverted hydrogen cyanide, (b) removing the at least one nickel(0) catalyst from the hydrocyanation stream 1 to obtain a catalyst stream 1 which comprises the at least one nickel(0) catalyst, and a hydrocyanation stream 2 which comprises 3-pentenenitrile, 2-pentenenitrile, 2-methyl-2-butenenitrile, 2-methyl-3-butenenitrile and $C_9$ nitrites, (c) regenerating the at least one nickel(0) catalyst in the catalyst stream 1 by reductive nickel catalyst synthesis with addition of fresh ligand to obtain a catalyst stream 2, (d) hydrocyanating 3-pentenenitrile over at least one nickel (0) catalyst and in the presence of at least one Lewis acid, the nickel(0) catalyst and the Lewis acid stemming at least partly from catalyst stream 2, resulting in a hydrocyanation stream 3 which comprises the at least one nickel(0) catalyst, adiponitrile and the at least one Lewis acid, (e) removing the at least one nickel(0) catalyst from the hydrocyanation stream 3 by extraction with an organic solvent to obtain a catalyst stream 3 which comprises the at least one nickel(0) catalyst, and a product stream which comprises adiponitrile, and the catalyst stream 3 can be recycled at least partly into process step (a).

In the context of the present invention, 2-pentenenitrile also refers to isomers of 2-pentenenitrile.

In the context of the present invention, 2-methyl-2-butenenitrile also refers to isomers of 2-methyl-2-butenenitrile.

Process step (a) comprises the reaction of 1,3-butadiene with hydrogen cyanide over at least one catalyst. The catalyst used is preferably a homogeneously dissolved catalyst. Particular preference is given to using homogeneously dissolved nickel(0) catalysts.

The nickel(0) catalyst complexes used with particular preference are preferably stabilized with phosphorus ligands.

The Ni(0) complexes which contain phosphorus ligands and/or free phosphorus ligands are preferably homogeneously dissolved nickel(0) complexes.

The phosphorus ligands of the nickel(0) complexes and the free phosphorus ligands are preferably selected from mono- or bidentate phosphines, phosphites, phosphinites and phosphonites.

These phosphorus ligands preferably have the formula I:

$$P(X^1R^1)(X^2R^2)(X^3R^3) \tag{I}$$

In the context of the present invention, compound I is a single compound or a mixture of different compounds of the aforementioned formula.

According to the invention, $X^1, X^2, X^3$ each independently are oxygen or a single bond. When all of the $X^1, X^2$ and $X^3$ groups are single bonds, compound I is a phosphine of the formula $P(R^1R^2R^3)$ with the definitions of $R^1, R^2$ and $R^3$ specified in this description.

When two of the $X^1, X^2$ and $X^3$ groups are single bonds and one is oxygen, compound I is a phosphinite of the formula $P(OR^1)(R^2)(R^3)$ or $P(R^1)(OR^2)(R^3)$ or $P(R^1)(R^2)(OR^3)$ with the definitions of $R^1, R^2$ and $R^3$ specified below.

When one of the $X^1, X^2$ and $X^3$ groups is a single bond and two are oxygen, compound I is a phosphonite of the formula $P(OR^1)(OR^2)(R^3)$ or $P(R^1)(OR^2)(OR^3)$ or $P(OR^1)(R^2)(OR^3)$ with the definitions of $R^1, R^2$ and $R^3$ specified in this description.

In a preferred embodiment, all $X^1, X^2$ and $X^3$ groups should be oxygen, so that compound I is advantageously a phosphite of the formula $P(OR^1)(OR^2)(OR^3)$ with the definitions of $R^1, R^2$ and $R^3$ specified below.

According to the invention, $R^1, R^2, R^3$ are each independently identical or different organic radicals. $R^1, R^2$ and $R^3$ are each independently alkyl radicals preferably having from 1 to 10 carbon atoms, such as methyl, ethyl, n-propyl, i-propyl, n-butyl, i-butyl, s-butyl, t-butyl, aryl groups such as phenyl, o-tolyl, m-tolyl, p-tolyl, 1-naphthyl, 2-naphthyl, or hydrocarbyl, preferably having from 1 to 20 carbon atoms, such as 1,1'-biphenol, 1,1'-binaphthol. The $R^1, R^2$ and $R^3$ groups may be bonded together directly, i.e. not solely via the central phosphorus atom. Preference is given to the $R^1$, $R^2$ and $R^3$ groups not being bonded together directly.

In a preferred embodiment, $R^1$, $R^2$ and $R^3$ groups are radicals selected from the group consisting of phenyl, o-tolyl, m-tolyl and p-tolyl. In a particularly preferred embodiment, a maximum of two of the $R^1$, $R^2$ and $R^3$ groups should be phenyl groups.

In another preferred embodiment, a maximum of two of the $R^1$, $R^2$ and $R^3$ groups should be o-tolyl groups.

Particularly preferred compounds I which may be used are those of the formula I a where w, x, y, z are each a natural number and the following conditions apply: $w+x+y+z=3$ and $w, z \leqq 2$.

Examples of such compounds I a are (p-tolyl-O—)(phenyl-O—)$_2$P, (m-tolyl-O—) (phenyl-O—)$_2$P, (o-tolyl-O—)(phenyl-O—)$_2$P, (p-tolyl-O—)$_2$(phenyl-O—)P, (m-tolyl-O—)$_2$(phenyl-O—)P, (o-tolyl-O—)$_2$(phenyl-O—)P, (m-tolyl-O—)(p-tolyl-O—)(phenyl-O—)P, (o-tolyl-O—)(p-tolyl-O—)(phenyl-O—)P, (o-tolyl-O—) (m-tolyl-O—)(phenyl-O—)P, (p-tolyl-O—)$_3$P, (m-tolyl-O—)(p-tolyl-O—)$_2$P, (o-tolyl-O—)(p-tolyl-O—)$_2$P, (m-tolyl-O—)$_2$(p-tolyl-O—)P, (o-tolyl-O—)$_2$(p-tolyl-O—)P, (o-tolyl-O—)(m-tolyl-O—)(p-tolyl-O—)P, (m-tolyl-O—)$_3$P, (o-tolyl-O—)(m-tolyl-O—)$_2$P, (o-tolyl-O—)$_2$(m-tolyl-O—)P or mixtures of such compounds.

Mixtures comprising (m-tolyl-O—)$_3$P, (m-tolyl-O—)$_2$(p-tolyl-O—)P, (m-tolyl-O—)(p-tolyl-O—)$_2$P and (p-tolyl-O—)$_3$P may be obtained, for example, by reacting a mixture comprising m-cresol and p-cresol, in particular in a molar ratio of 2:1, as obtained in the distillative workup of crude oil, with a phosphorus trihalide, such as phosphorus trichloride.

In another, likewise preferred embodiment, the phosphorus ligands are the phosphites, described in detail in DE-A 199 53 058, of the formula I b:

where $R^1$: aromatic radical having a $C_1$-$C_{18}$-alkyl substituent in the o-position to the oxygen atom which joins the phosphorus atom to the aromatic system, or having an aromatic substituent in the o-position to the oxygen atom which joins the phosphorus atom to the aromatic system, or having a fused aromatic system in the o-position to the oxygen atom which joins the phosphorus atom to the aromatic system, $R^2$: aromatic radical having a $C_1$-$C_{18}$-alkyl substituent in the m-position to the oxygen atom which joins the phosphorus atom to the aromatic system, or having an aromatic substituent in the m-position to the oxygen atom which joins the phosphorus atom to the aromatic system, or having a fused aromatic system in the m-position to the oxygen atom which joins the phosphorus atom to the aromatic system, the aromatic radical bearing a hydrogen atom in the o-position to the oxygen atom which joins the phosphorus atom to the aromatic system, $R^3$: aromatic radical having a $C_1$-$C_{18}$-alkyl substituent in the p-position to the oxygen atom which joins the phosphorus atom to the aromatic system, or having an aromatic substituent in the p-position to the oxygen atom which joins the phosphorus atom to the aromatic system, the aromatic radical bearing a hydrogen atom in the o-position to the oxygen atom which joins the phosphorus atom to the aromatic system, $R^4$: aromatic radical which bears substituents other than those defined for $R^1$, $R^2$ and $R^3$ in the o-, m- and p-position to the oxygen atom which joins the phosphorus atom to the aromatic system, the aromatic radical bearing a hydrogen atom in the o-position to the oxygen atom which joins the phosphorus atom to the aromatic system, x: 1 or 2, y, z, p: each independently 0, 1 or 2, with the proviso that $x+y+z+p=3$.

Preferred phosphites of the formula I b can be taken from DE-A 199 53 058. The $R^1$ radical may advantageously be o-tolyl, o-ethylphenyl, o-n-propylphenyl, o-isopropyl-phenyl, o-n-butylphenyl, o-sec-butylphenyl, o-tert-butylphenyl, (o-phenyl)phenyl or 1-naphthyl groups.

Preferred $R^2$ radicals are m-tolyl, m-ethylphenyl, m-n-propylphenyl, m-isopropylphenyl, m-n-butylphenyl, m-sec-butylphenyl, m-tert-butylphenyl, (m-phenyl)phenyl or 2-naphthyl groups.

Advantageous $R^3$ radicals are p-tolyl, p-ethylphenyl, p-n-propylphenyl, p-isopropyl-phenyl, p-n-butylphenyl, p-sec-butylphenyl, p-tert-butylphenyl or (p-phenyl)phenyl groups.

The $R^4$ radical is preferably phenyl. p is preferably zero. For the indices x, y, z and p in compound I b, there are the following possibilities:

| x | y | z | p |
|---|---|---|---|
| 1 | 0 | 0 | 2 |
| 1 | 0 | 1 | 1 |
| 1 | 1 | 0 | 1 |
| 2 | 0 | 0 | 1 |
| 1 | 0 | 2 | 0 |
| 1 | 1 | 1 | 0 |
| 1 | 2 | 0 | 0 |
| 2 | 0 | 1 | 0 |
| 2 | 1 | 0 | 0 |

Preferred phosphites of the formula I b are those in which p is zero, and $R^1$, $R^2$ and $R^3$ are each independently selected from o-isopropylphenyl, m-tolyl and p-tolyl, and $R^4$ is phenyl.

Particularly preferred phosphites of the formula I b are those in which $R^1$ is the o-isopropylphenyl radical, $R^2$ is the m-tolyl radical and $R^3$ is the p-tolyl radical with the indices specified in the table above; also those in which $R^1$ is the o-tolyl radical, $R^2$ is the m-tolyl radical and $R^3$ is the p-tolyl radical with the indices specified in the table; additionally those in which $R^1$ is the 1-naphthyl radical, $R^2$ is the m-tolyl radical and $R^3$ is the p-tolyl radical with the indices specified in the table; also those in which $R^1$ is the o-tolyl radical, $R^2$ is the 2-naphthyl radical and $R^3$ is the p-tolyl radical with the indices specified in the table; and finally those in which $R^1$ is the o-isopropylphenyl radical, $R^2$ is the 2-naphthyl radical and $R^3$ is the p-tolyl radical with the indices specified in the table; and also mixtures of these phosphites.

Phosphites of the formula I b may be obtained by a) reacting a phosphorus trihalide with an alcohol selected from the group consisting of $R^1OH$, $R^2OH$, $R^3OH$ and $R^4OH$ or mixtures thereof to obtain a dihalophosphorous monoester, b) reacting the dihalophosphorous monoester mentioned with an alcohol selected from the group consisting of $R^{10}H$, $R^2OH$, $R^{30}H$ and $R^4OH$ or mixtures thereof to obtain a monohalophosphorous diester and c) reacting the monohalophosphorous diester mentioned with an alcohol selected from the group consisting of $R^1OH$, $R^2OH$, $R^3OH$ and $R^4OH$ or mixtures thereof to obtain a phosphite of the formula I b.

The reaction may be carried out in three separate steps. Equally, two of the three steps may be combined, i.e. a) with b) or b) with c). Alternatively, all of steps a), b) and c) may be combined together.

Suitable parameters and amounts of the alcohols selected from the group consisting of $R^1OH$, $R^2OH$, $R^3OH$ and $R^4OH$ or mixtures thereof may be determined readily by a few simple preliminary experiments.

Useful phosphorus trihalides are in principle all phosphorus trihalides, preferably those in which the halide used is Cl, Br, I, in particular Cl, and mixtures thereof. It is also possible to use mixtures of various identically or differently halogen-substituted phosphines as the phosphorus trihalide. Particular preference is given to $PCl_3$. Further details on the reaction conditions in the preparation of the phosphites I b and for the workup can be taken from DE-A 199 53 058.

The phosphites I b may also be used in the form of a mixture of different phosphites I b as a ligand. Such a mixture may be obtained, for example, in the preparation of the phosphites I b.

However, preference is given to the phosphorus ligand being multidentate, in particular bidentate. The ligand used therefore preferably has the formula II where $X^{11}, X^{12}, X^{13}, X^{21}, X^{22}, X^{23}$ are each independently oxygen or a single bond $R^{11}, R^{12}$ are each independently identical or different, separate or bridged organic radicals $R^{21}, R^{22}$ are each independently identical or different, separate or bridged organic radicals, Y is a bridging group.

In the context of the present invention, compound II is a single compound or a mixture of different compounds of the aforementioned formula.

In a preferred embodiment, $X^{11}, X^{12}, X^{13}, X^{21}, X^{22}, X^{23}$ may each be oxygen. In such a case, the bridging group Y is bonded to phosphite groups.

In another preferred embodiment, $X^{11}$ and $X^{12}$ may each be oxygen and $X^{13}$ a single bond, or $X^{11}$ and $X^{13}$ each oxygen and $X^{12}$ a single bond, so that the phosphorus atom surrounded by $X^{11}, X^{12}$ and $X^{13}$ is the central atom of a phosphonite. In such a case, $X^{21}, X^{22}$ and $X^{23}$ may each be oxygen, or $X^{21}$ and $X^{22}$ may each be oxygen and $X^{23}$ a single bond, or $X^{21}$ and $X^{23}$ may each be oxygen and $X^{22}$ a single bond, or $X^{23}$ may be oxygen and $X^{21}$ and $X^{22}$ each a single bond, or $X^{21}$ may be oxygen and $X^{22}$ and $X^{23}$ each a single bond, or $X^{21}, X^{22}$ and $X^{23}$ may each be a single bond, so that the phosphorus atom surrounded by $X^{21}, X^{22}$ and $X^{23}$ may be the central atom of a phosphite, phosphonite, phosphinite or phosphine, preferably a phosphonite.

In another preferred embodiment, $X^{13}$ may be oxygen and $X^{11}$ and $X^{12}$ each a single bond, or $X^{11}$ may be oxygen and $X^{12}$ and $X^{13}$ each a single bond, so that the phosphorus atom surrounded by $X^{11}, X^{12}$ and $X^{13}$ is the central atom of a phosphonite. In such a case, $X^{21}, X^{22}$ and $X^{23}$ may each be oxygen, or $X^{23}$ may be oxygen and $X^{21}$ and $X^{22}$ each a single bond, or $X^{21}$ may be oxygen and $X^{22}$ and $X^{23}$ each a single bond, or $X^{21}, X^{22}$ and $X^{23}$ may each be a single bond, so that the phosphorus atom surrounded by $X^{21}, X^{22}$ and $X^{23}$ may be the central atom of a phosphite, phosphinite or phosphine, preferably a phosphinite.

In another preferred embodiment, $X^{11}, X^{12}$ and $X^{13}$ may each be a single bond, so that the phosphorus atom surrounded by $X^{11}, X^{12}$ and $X^{13}$ is the central atom of a phosphine. In such a case, $X^{21}, X^{22}$ and $X^{23}$ may each be oxygen, or $X^{21}, X^{22}$ and $X^{23}$ may each be a single bond, so that the phosphorus atom surrounded by $X^{21}, X^{22}$ and $X^{23}$ may be the central atom of a phosphite or phosphine, preferably a phosphine. The bridging group Y is preferably an aryl group which is substituted, for example by $C_1$-$C_4$-alkyl, halogen, such as fluorine, chlorine, bromine, halogenated alkyl, such as trifluoromethyl, aryl, such as phenyl, or is unsubstituted, preferably a group having from 6 to 20 carbon atoms in the aromatic system, in particular pyrocatechol, bis(phenol) or bis(naphthol).

The $R^{11}$ and $R^{12}$ radicals may each independently be identical or different organic radicals. Advantageous $R^{11}$ and $R^{12}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{21}$ and $R^{22}$ radicals may each independently be identical or different organic radicals. Advantageous $R^{21}$ and $R^{22}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{11}$ and $R^{12}$ radicals may each be separate or bridged. The $R^{21}$ and $R^{22}$ radicals may also each be separate or bridged. The $R^{11}$, $R^{12}$, $R^{21}$ and $R^{22}$ radicals may each be separate, two may be bridged and two separate, or all four may be bridged, in the manner described.

In a particularly preferred embodiment, useful compounds are those of the formula I, II, III, IV and V specified in U.S. Pat. No. 5,723,641. In a particularly preferred embodiment, useful compounds are those of the formula I, II, III, IV, V, VI and VII specified in U.S. Pat. No. 5,512,696, in particular the compounds used there in examples 1 to 31. In a particularly preferred embodiment, useful compounds are those of the formula I, II, III, IV, V, VI, VII, VIII, IX, X, XI, XII, XIII, XIV and XV specified in U.S. Pat. No. 5,821,378, in particular the compounds used there in examples 1 to 73.

In a particularly preferred embodiment, useful compounds are those of the formula I, II, III, IV, V and VI specified in U.S. Pat. No. 5,512,695, in particular the compounds used there in examples 1 to 6. In a particularly preferred embodiment, useful compounds are those of the formula I, II, III, IV, V, VI, VII, VIII, IX, X, XI, XII, XIII and XIV specified in U.S. Pat. No. 5,981,772, in particular the compounds used there in examples 1 to 66.

In a particularly preferred embodiment, useful compounds are those specified in U.S. Pat. No. 6,127,567 and the compounds used there in examples 1 to 29. In a particularly preferred embodiment, useful compounds are those of the formula I, II, III, IV, V, VI, VII, VIII, IX and X specified in U.S. Pat. No. 6,020,516, in particular the compounds used there in examples 1 to 33. In a particularly preferred embodiment, useful compounds are those specified in U.S. Pat. No. 5,959,135, and the compounds used there in examples 1 to 13.

In a particularly preferred embodiment, useful compounds are those of the formula I, II and III specified in U.S. Pat. No. 5,847,191. In a particularly preferred embodiment, useful compounds are those specified in U.S. Pat. No. 5,523,453, in particular the compounds illustrated there in formula 1, 2, 3, 4, 5, 6, 7, 8, 9, 10, 11, 12, 13, 14, 15, 16, 17, 18, 19, 20, and 21. In a particularly preferred embodiment, useful compounds are those specified in WO 01/14392, preferably the compounds illustrated there in formula V, VI, VII, VIII, IX, X, XI, XII, XIII, XIV, XV, XVI, XVII, XXI, XXII, XXIII.

In a particularly preferred embodiment, useful compounds are those specified in WO 98/27054. In a particularly preferred embodiment, useful compounds are those specified in WO 99/13983. In a particularly preferred embodiment, useful compounds are those specified in WO 99/64155.

In a particularly preferred embodiment, useful compounds are those specified in the German patent application DE 100 380 37. In a particularly preferred embodiment, useful compounds are those specified in the German patent application DE 100 460 25. In a particularly preferred embodiment, useful compounds are those specified in the German patent application DE 101 502 85.

In a particularly preferred embodiment, useful compounds are those specified in the German patent application DE 101 502 86. In a particularly preferred embodiment, useful compounds are those specified in the German patent application DE 102 071 65. In a further particularly preferred embodiment of the present invention, useful phosphorus chelate ligands are those specified in US 2003/0100442 A1.

In a further particularly preferred embodiment of the present invention, useful phosphorus chelate ligands are those specified in the German patent application reference number DE 103 50 999.2 of Dec. 30, 2003 which has an earlier priority date but had not been published at the priority date of the present application.

The compounds I, I a, I b and II described and their preparation are known per se. Phosphorus ligands used may also be mixtures comprising at least two of the compounds I, I a, I b and II.

In a particularly preferred embodiment of the process according to the invention, the phosphorus ligand of the nickel(0) complex and/or the free phosphorus ligand is selected from tritolyl phosphite, bidentate phosphorus chelate ligands and the phosphites of the formula I b (I b)

where $R^1$, $R^2$ and $R^3$ are each independently selected from o-isopropylphenyl, m-tolyl and p-tolyl, $R^4$ is phenyl; x is 1 or 2, and y, z, p are each independently 0, 1 or 2 with the proviso that $x+y+z+p=3$; and mixtures thereof.

The hydrocyanation may be carried out in the presence or in the absence of a solvent. When a solvent is used, the solvent should be liquid at the given reaction temperature and the given reaction pressure and inert toward the unsaturated compounds and the at least one catalyst. In general, the solvents used are hydrocarbons, for example benzene or xylene, or nitriles, for example acetonitrile or benzonitrile. However, preference is given to using a ligand as the solvent. It is also possible to use a plurality of, such as two or three, solvents.

The catalysts used in process step (a) may be prepared, for example, by reductive catalyst synthesis. To this end, a nickel (II) source is reacted with ligand by commonly known processes, as described, for example, in U.S. Pat. No. 6,127,567 and the references cited therein, and also the German patent applications DE 103 51 000.1, DE 103 51 002.8 and DE 103 51 003.6 to BASF AG to give the nickel(0) complex.

Process step (a) of the process according to the invention may be carried out in any suitable apparatus known to those skilled in the art. Useful apparatus for the reaction is that which is customary for this purpose, as described, for example, in: Kirk-Othmer, Encyclopedia of Chemical Technology, 4th Ed. Vol. 20, John Wiley & Sons, New York 1996, pages 1040 to 1055, such as stirred tank reactors, loop reactors, gas circulation reactors, bubble column reactors or tubular reactors, in each case if appropriate with apparatus to remove heat of reaction. The reaction may be carried out in a plurality of, such as two or three, apparatuses.

In a preferred embodiment of the process according to the invention, advantageous reactors have been found to be those having backmixing characteristics or batteries of reactors having backmixing characteristics. It has been found that particularly advantageous batteries of reactors having backmixing characteristics have been found to be those which are operated in crossflow mode with regard to the metering of hydrogen cyanide.

The reaction may be carried out in batch mode, continuously or in semibatchwise operation.

Preference is given to carrying out the hydrocyanation continuously in one or more stirred process steps. When a plurality of process steps is used, preference is given to the process steps being connected in series. In that case, the product is transferred from one process step directly into the next process step. The hydrogen cyanide may be fed directly into the first process step or between the individual process steps.

When the process according to the invention is carried out in semibatchwise operation, it is preferred that the reactor is initially charged with the catalyst components and 1,3-butadiene, while hydrogen cyanide is metered into the reaction mixture over the reaction time.

The hydrocyanation reaction may be carried out by charging the apparatus with all reactants. However, it is preferred that the apparatus is filled with the at least one catalyst, 1,3-butadiene and, if appropriate, the solvent. The gaseous hydrogen cyanide preferably floats over the surface of the reaction mixture or is passed through the reaction mixture. A further procedure for charging the apparatus is the filling of the apparatus with the at least one catalyst, hydrogen cyanide and, if appropriate, the solvent, and slowly metering the 1,3-butadiene into the reaction mixture. Alternatively, it is also possible that the reactants are introduced into the reactor and the reaction mixture is brought to the reaction temperature at which the hydrogen cyanide is added to the mixture in liquid form. In addition, the hydrogen cyanide may also be added before heating to reaction temperature. The reaction is carried out under conventional hydrocyanation conditions for temperature, atmosphere, reaction time, etc.

The reaction is preferably carried out at pressures of from 0.1 to 500 MPa, more preferably from 0.5 to 50 MPa, in particular from 1 to 5 MPa. The reaction is preferably carried out at temperatures of from 273 to 473 K, more preferably from 313 to 423 K, in particular from 333 to 393 K. Advantageous average mean residence times of the liquid reactor phase have been found to be in the range from 0.001 to 100 hours, preferably from 0.05 to 20 hours, more preferably from 0.1 to 5 hours, per reactor.

In one embodiment, the reaction may be performed in the liquid phase in the presence of a gas phase and, if appropriate, of a solid suspended phase. The starting materials, hydrogen cyanide and 1,3-butadiene, may each be metered in liquid or gaseous form.

In a further embodiment, the reaction may be carried out in the liquid phase, in which case the pressure in the reactor is such that all feedstocks such as 1,3-butadiene, hydrogen cyanide and the at least one catalyst are metered in liquid form and are in the liquid phase in the reaction mixture. A solid suspended phase may be present in the reaction mixture and may also be metered in together with the at least one catalyst, for example consisting of degradation products of the catalyst system comprising nickel(II) compounds inter alia.

In process step (a), a hydrocyanation stream 1 is obtained which comprises 3-pentenenitrile, 2-pentenenitrile, 2-methyl-2-butenenitrile, $C_9$ nitrites, 2-methyl-3-butenenitrile, the at least one nickel(0) catalyst, methylglutaronitrile, unconverted 1,3-butadiene and residues of unconverted hydrogen cyanide. This hydrocyanation stream 1 preferably contains from 1 to 80% by weight, more preferably from 10 to 50% by weight, of the at least one catalyst, from 0.1 to 50% by weight, more preferably from 1 to 25% by weight, of 1,3-butadiene, from 1 to 80% by weight, more preferably from 10 to 50% by weight, of pentenenitriles comprising trans-3-pentenenitrile, 2-methyl-3-butenenitrile and also further pentenenitrile isomers, and from 0.1 ppm by weight to 10% by weight, more preferably from 10 ppm by weight to 1% by weight, of hydrogen cyanide, and less than 5% by weight, more preferably less than 4% by weight, of methylglutaronitrile. The amount of $C_9$ nitriles is preferably small.

The hydrocyanation stream 1 which comprises 3-pentenenitrile, 2-methyl-3-butenenitrile, 2-pentenenitrile, $C_9$ nitrites, methylglutaronitrile and the at least one catalyst is subsequently transferred into process step (b).

In this process step (b), the at least one nickel(0) catalyst is removed from the hydrocyanation stream 1. This provides a catalyst stream 1 which comprises the at least one nickel(0) catalyst. In addition, a hydrocyanation stream 2 is obtained which comprises 3-pentenenitrile, 2-pentenenitrile, 2-methyl-2-butenenitrile, $C_9$ nitrites, 2-methyl-3-butenenitrile and methylglutaronitrile. The removal of the at least one nickel(0) catalyst is preferably effected by distillation.

The removal of the at least one nickel(0) catalyst from the hydrocyanation stream 1 by distillation may be carried out in any suitable apparatus known to those skilled in the art. Suitable apparatus for distillation is as described, for example, in: Kirk-Othmer, Encyclopedia of Chemical Technology, 4th Ed., Vol. 8, John Wiley & Sons, New York, 1996, pages 334 to 338, such as sieve tray columns, bubble-cap tray columns, columns having structured packing or random packing, which may also be operated as dividing wall columns. This distillation apparatus is preferably equipped in each case with suitable apparatus for evaporation, such as falling-film evaporators, thin-film evaporators, multiphase helical tube evaporators, natural circulation evaporators or forced circulation flash evaporators, and also with apparatus for condensing the vapor stream. The distillation may be carried out in a plurality of, such as two or three, apparatuses. The distillation may be effected in one stage in the case of a partial evaporation of the feed stream. Particular preference is given to embodiments in which the bottom temperatures of the distillation apparatuses are all smaller than 140° C., preferably smaller than 130° C., more preferably smaller than 120° C. Further preferred embodiments provide for a sum of the average residence times in the bottom of the distillation apparatuses of at most 10 hours, more preferably at most 5 hours, in particular at most 1 hour. Especially preferred are embodiments which fulfill the two features detailed above simultaneously. The embodiments feature particularly gentle catalyst handling.

The at least one nickel(0) catalyst removed in process step (b) in catalyst stream 1 is then subsequently regenerated in a process step (c) by reductive nickel catalyst synthesis, if appropriate with addition of fresh ligand and with addition of additional Lewis acid.

The regeneration of the at least one nickel(0) catalyst may be carried out in any suitable apparatus known to those skilled in the art. Suitable apparatus is, for example, that which is customary for this purpose, which is described, for example, in: Kirk-Othmer, Encyclopedia of Chemical Technology, 4th Ed., Vol 20, John Wiley & Sons, New York, 1996, pages 1040 to 1055, such as stirred tank reactors, loop reactors, gas circulation reactors, bubble column reactors or tubular reactors. The reaction may also be carried out in a plurality of, for example 2 or 3, apparatuses.

A preferred embodiment of the reductive nickel catalyst synthesis is described in the German patent application DE 103 51 000.1, which has an earlier priority date but had not been published at the priority date of the present application, with the title "Preparation of nickel(0)-phosphorus ligand complexes" to BASF AG. According to this, the nickel(0) catalyst is prepared by reducing a nickel(II)-ether adduct in the presence of at least one phosphorus ligand. The nickel(II)-ether adduct to be used for this process is preferably prepared by dissolving a nickel halide in water, admixing with an ether and an organic nitrile, if appropriate with stirring, and subsequently removing water and, if appropriate, ether. The nickel (II)-ether adduct is preferably anhydrous and, in a preferred embodiment, comprises a nickel halide. Useful nickel halides are nickel chloride, nickel bromide and nickel iodide. Preference is given to nickel chloride. The nickel(II)-ether adduct used preferably comprises an oxygen-containing, sulfur-containing or mixed oxygen/sulfur-containing ether. This is preferably selected from the group consisting of tetrahydrofuran, dioxane, diethyl ether, di-n-propyl ether, diisopropyl ether, di-n-butyl ether, di-sec-butyl ether, ethylene glycol dialkyl ether, diethylene glycol dialkyl ether and triethylene glycol dialkyl ether. The ethylene glycol dialkyl ether used is preferably ethylene glycol dimethyl ether (1,2-dimethoxyethane, glyme) and ethylene glycol diethyl ether. The diethylene glycol dialkyl ether used is preferably diethylene glycol dimethyl ether (diglyme). The triethylene glycol dialkyl ether used is preferably triethylene glycol dimethyl ether (triglyme). The reducing agent used to prepare the nickel(0) complex is preferably selected from the group consisting of metals which are more electropositive than nickel, metal alkyls, electrical current, complex hydrides and hydrogen.

In a further embodiment, the nickel(0) catalyst may be prepared by a process which is described in the German patent application DE 103 51 002.8, which has an earlier priority date but had not been published at the priority date of the present application, with the title "Preparation of nickel (0)-phosphorus ligand complexes" to BASF AG. According to this, the nickel(0) complex is prepared by reducing a nickel (II) source which comprises nickel bromide, nickel iodide or mixtures thereof in the presence of at least one phosphorus ligand. The nickel(II) source is preferably used without preceding special drying. It is preferred that the preparation is effected preferably in a solvent which is selected from the group consisting of organic nitriles, aromatic or aliphatic hydrocarbons or mixtures thereof. The reducing agents used are preferably metals which are more electropositive than nickel. It is likewise also possible to use metal alkyls, electrical current, complex hydrides or hydrogen.

In addition, the nickel(0) catalyst used in the process according to the invention may also be prepared by a process which is described in the German patent application DE 103 51 003.6, which has an earlier priority date but had not been published at the priority date of the present application, with the title "Use of azeotropically dried nickel(II) halides" to BASF AG. According to this, the nickel(0) complex is prepared by reducing an aqueous nickel(II) halide, dried by azeotropic distillation if it previously contained water, in the presence of at least one phosphorus ligand. The nickel(II) halide is preferably selected from the group consisting of nickel(II) chloride, nickel(II) bromide and nickel(II) iodide. The nickel(II) halide dried by azeotropic distillation is preferably prepared by a process for removing water from the corresponding aqueous nickel(II) halides, wherein the mixture is admixed with a diluent whose boiling point, in the case that the diluent mentioned does not form an azeotrope with water under the pressure conditions of the distillation mentioned below, is higher than the boiling point of water and which is present in liquid form at this boiling point of water, or which forms an azeotrope or heteroazeotrope with water under the pressure and temperature conditions of the distillation mentioned below, and the mixture comprising the aqueous nickel(II) halide and the diluent is distilled with removal of water or of the azeotrope mentioned or of the heteroazeotrope mentioned from this mixture to obtain an anhydrous mixture comprising nickel(II) halide and the said diluent. The mixture may in some cases be a suspension. The mixture is characterized by a residual content of water of less than 1000 ppm by weight, more preferably less than 500 ppm by weight, especially less than 100 ppm by weight. The diluent used is preferably an organic diluent having at least one nitrile group, preferably pentenenitrile. The reduction for the preparation of the corresponding nickel(0) complex is preferably effected by metals which are more electropositive than nickel. Alternatively, it is also possible to use metal alkyls, electrical current, metal hydrides and hydrogen.

The ligand used in the processes according to the above-described patent applications DE 103 51 000.1, DE 10351 002.8 and DE 10351 003.6 may also be present in a ligand solution which has already been used as a catalyst solution in hydrocyanation reactions, and is thus depleted in nickel(0).

In the context of the present invention, a Lewis acid refers to a single Lewis acid or a mixture of a plurality of, such as 2, 3 or 4, Lewis acids.

Useful Lewis acids are inorganic or organic metal compounds in which the cation is selected from the group consisting of scandium, titanium, vanadium, chromium, manganese, iron, cobalt, copper, zinc, boron, aluminum, yttrium, zirconium, niobium, molybdenum, cadmium, rhenium and tin. Examples include $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2$, $FeCl_2(THF)_2$, $TiCl_4(THF)_2$, $TiCl_4$, $TiCl_3$, $ClTi(O\text{-isopropyl})_3$, $MnCl_2$, $ScCl_3$, $AlCl_3$, $(C_8H_{17})AlCl_2$, $(C_8H_{17})_2AlCl$, $(i\text{-}C_4H_9)_2AlCl$, $(C_6H_5)_2AlCl$, $(C_6H_5)AlCl_2$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $B(C_6H_5)_3$, $TaCl_5$, as described, for example, in U.S. Pat. Nos. 6,127,567, 6,171, 996 and 6,380,421. Also useful are metal salts such as $ZnCl_2$, $CoI_2$ and $SnCl_2$, and organometallic compounds such as $RAlCl_2$, $R_2AlCl$, $RSnO_3SCF_3$ and $R_3B$, where R is an alkyl or aryl group, as described, for example, in U.S. Pat. Nos. 3,496, 217, 3,496,218 and 4,774,353. According to U.S. Pat. No. 3,773,809, the promoter used may also be a metal in cationic form which is selected from the group consisting of zinc, cadmium, beryllium, aluminum, gallium, indium, thallium, titanium, zirconium, hafnium, erbium, germanium, tin, vanadium, niobium, scandium, chromium, molybdenum, tungsten, manganese, rhenium, palladium, thorium, iron and cobalt, preferably zinc, cadmium, titanium, tin, chromium, iron and cobalt, and the anionic moiety of the compound may be selected from the group consisting of halides such as fluoride, chloride, bromide and iodide, anions of lower fatty acids having from 2 to 7 carbon atoms, $HPO_3^{2-}$, $H_3PO^{2-}$, $CF_3COO^-$, $C_7H_{15}OSO_2^-$ or $SO_4^{2-}$. Further suitable promoters, disclosed by U.S. Pat. No. 3,773,809, are borohydrides, organoborohydrides and boric esters of the formula $R_3B$ and $B(OR)_3$, where R is selected from the group consisting of hydrogen, aryl radicals having from 6 to 18 carbon atoms, aryl radicals substituted by alkyl groups having from 1 to 7 carbon atoms and aryl radicals substituted by cyano-substituted alkyl groups having from 1 to 7 carbon atoms, advantageously triphenylboron. Moreover, as described in U.S. Pat. No. 4,874,884, it is possible to use synergistically active combinations of Lewis acids, in order to increase the activity of the catalyst system. Suitable promoters may, for example, be selected from the group consisting of $CdCl_2$, $FeCl_2$, $ZnCl_2$, $B(C_6H_5)_3$ and $(C_6H_5)_3SnX$ where $X=CF_3SO_3$, $CH_3C_6H_4SO_3$ or $(C_6H_5)_3BCN$, and the preferred ratio specified of promoter to nickel is from about 1:16 to about 50:1.

In the context of the present invention, the term Lewis acid also includes the promoters specified in U.S. Pat. Nos. 3,496, 217, 3,496,218, 4,774,353, 4,874,884, 6,127,567, 6,171,996 and 6,380,421.

Particularly preferred Lewis acids among those mentioned are in particular metal salts, more preferably metal halides, such as fluorides, chlorides, bromides, iodides, in particular chlorides, of which particular preference is given in turn to zinc chloride, iron(II) chloride and iron(III) chloride.

In the preferred embodiment of the process according to the invention, 3-pentenenitrile is subsequently hydrocyanated in a process step (d) over a nickel(0) catalyst and in the presence of a Lewis acid, the nickel(0) catalyst and the Lewis acid stemming at least partly from the catalyst stream 2. This provides a hydrocyanation stream 3. This comprises the at least one nickel(0) catalyst, adiponitrile and the at least one Lewis acid.

Advantageous conditions of the hydrocyanation of 3-pentenenitrile can be taken from U.S. Pat. Nos. 6,127,567 and 5,693,843, whose contents on this subject are incorporated by reference into the present invention.

Process step (d) may be carried out in any suitable apparatus known to those skilled in the art. Useful apparatus for the reaction is thus customary apparatus, as described, for example, in: Kirk-Othmer, Encyclopedia of Chemical Technology, 4th Ed., Vol. 20, John Wiley & Sons, New York, 1996, pages 1040 to 1055, such as stirred tank reactors, loop reactors, gas circulation reactors, bubble column reactors or tubular reactors, in each case if appropriate with apparatus for removing heat of reaction. The reaction may be carried out in a plurality of, such as two or three, apparatuses.

In a preferred embodiment of the process according to the invention, advantageous reactors have been found to be those having backmixing characteristics or batteries of reactors having backmixing characteristics. Particularly advantageous batteries of reactors having backmixing characteristics have been found to be those which are operated in crossflow mode in relation to the metering of hydrogen cyanide.

If appropriate, it is also possible for only a portion of the catalyst stream 2 to be used in the hydrocyanation of process step (d). The remaining portion is then conducted directly into process step (e) as a bypass stream 1.

In a subsequent process step (e), the at least one nickel(0) catalyst is preferably removed from the hydrocyanation stream 3. This is effected preferably by extraction with an organic solvent. This provides a catalyst stream 3 which comprises at least one nickel catalyst, and a product stream which comprises adiponitrile.

Process step (e) may be carried out in any suitable apparatus known to those skilled in the art. The extraction of process step (e) takes place preferably in countercurrent extraction columns, mixer-settler units or combinations of mixer-settler units with columns. Particular preference is given to using countercurrent extraction columns which are equipped especially with sheet metal packings as dispersing elements. This is surprising, since the hydrocyanation effluent is solids-laden. It has been found in accordance with the invention that the nickel(II) cyanide-containing solid which is formed in the hydrocyanation steps (a) and/or (d), contrary to expectations, does not have a tendency to cause fouling under the conditions in the extraction and does not form any noticeable deposits on column internals.

In a further particularly preferred embodiment, the countercurrent extraction is performed in a compartmented, stirred extraction column.

In a preferred embodiment, the extractant is used as the disperse phase and the hydrocyanation stream 3 as the continuous phase.

In the extraction, a phase ratio of from 0.1 to 10, calculated as the ratio of volume of the extractant supplied to volume of the mixture to be extracted, may be used. In a preferred embodiment, the extraction is operated with a phase ratio of from 0.4 to 2.5, in a preferred embodiment from 0.75 to 1.5.

The absolute pressure in process step (e) is preferably from 0.1 to 10 bar, more preferably from 0.5 to 5 bar, in particular from 1.0 to 2.5 bar. The extraction is carried out preferably at temperatures of from −15 to 120° C., more preferably from 0 to 60° C., in particular from 25 to 45° C.

In a preferred embodiment of the present invention, the extractant is selected from the group consisting of cyclohexane, methylcyclohexane, n-hexane, n-heptane, isomeric C6-, C7-, C8-, C9-cycloaliphatics, isomeric C6-, C7-, C8-, C9-isoaliphatics, cis-, trans-decahydronaphthalene and mixtures thereof.

In a particularly preferred embodiment, the extractant used is cyclohexane, methylcyclohexane or mixtures thereof. Substantially no Lewis acid gets into the catalyst phase. In this context, substantially means that the residual concentration of the Lewis acid in the catalyst phase is preferably less than 3% by weight, more preferably less than 2% by weight, in particular less than 0.5% by weight, based on the catalyst phase after the extraction, even though the particularly preferred chelate ligands complex with the Lewis acid and can draw it into the nonpolar catalyst phase in the extraction.

The extractant used is preferably anhydrous, anhydrous meaning in the context of the present invention that the extractant contains less than 100 ppm, preferably less than 50 ppm, in particular less than 10 ppm, of water. The extractant may be dried by suitable processes known to those skilled in the art, for example by adsorption or azeotropic distillation.

The extractant is preferably dried by azeotropic distillation in a separate process step. This is effected preferably distillatively as a heteroazeotropic distillation. The absolute pressure in this process step is preferably from 0.01 to 10.0 bar, more preferably from 0.05 to 5.0 bar, in particular from 0.1 to 1.0 bar. The distillation is carried out in such a way that the temperature in the bottom of the distillation apparatus is preferably from 40 to 250° C., more preferably from 50 to 180° C., in particular from 60 to 150° C. The distillation is carried out in such a way that the temperature at the top of the distillation apparatus is preferably from 0 to 200° C., more preferably from 5 to 100° C., in particular from 20 to 50° C. In a preferred embodiment of the process according to the invention, the aforementioned temperature ranges are maintained both at the top and in the bottom of the distillation apparatus. The azeotropic distillation of the extractant is effected preferably in a distillation column having especially bubble-cap trays, structured sheet metal packings, structured fabric packings, dual-flow trays or beds of random packings as separating internals, if appropriate in a dividing wall column with side draws optionally present, a phase separator at the liquid draw of the top condenser for removing water, with apparatus for separate recycling of organic phases as reflux to columns, and also further apparatus suitable for azeotropic distillation.

In the process according to the invention, it is additionally preferred that the nickel(0) catalyst which is obtained in process step (e) and is present in the catalyst stream 3 is recycled at least partly into process step (a). It is advantageous here that the Lewis acid in process step (e) is removed substantially fully from the nickel(0) catalyst, since a remaining Lewis acid in a hydrocyanation of 1,3-butadiene leads to disproportionate formation of the methylglutaronitrile by-product. This would reduce the overall selectivity of the process.

It is advantageous to use a fresh or reductively regenerated catalyst for the process according to the invention initially in the hydrocyanation of 3-pentenenitrile, since a Lewis acid is required in this stage and the Lewis acid is formed as a by-product of the reductive catalyst synthesis, for example from a mixture of nickel halide or nickel halide-solvent adducts, preferably selected from the group consisting of nickel chloride, nickel bromide, nickel iodide, more preferably nickel chloride, and a reducing metal, preferably selected from the group consisting of zinc and iron. On this subject, reference is made to the German patent applications already mentioned, DE 103 51 000.1, DE 103 51 002.8 and DE 103 51 003.6 to BASF AG.

It is therefore particularly preferred that the process sequence begins with process step (d) in the first run when fresh Lewis acid and fresh nickel(0) catalyst and/or reductively regenerated nickel(0) catalyst are used.

It is particularly preferred that the 3-pentenenitrile hydrocyanated in process step (d) stems from the hydrocyanation stream 1.

In a further preferred embodiment of the process according to the invention, the hydrocyanation stream 1 stemming from process step (a) is subjected additionally to an isomerization step (a') before process step (b). In this step, 2-methyl-3-butenenitrile, which is formed as an undesired by-product in the hydrocyanation of 1,3-butadiene and is present in the hydrocyanation stream 1, is isomerized to 3-pentenenitrile over at least one nickel(0) catalyst. This forms a 2-methyl-3-butenenitrile-depleted and a 3-pentenenitrile-enriched isomerization stream 1. The thus obtained 3-pentenenitrile-enriched isomerization stream 1 is subsequently used in process step (b) instead of the hydrocyanation stream 1.

The nickel(0) catalyst used for the isomerization of 2-methyl-3-butenenitrile may be a nickel(0) catalyst as described above for the hydrocyanation of 1,3-butadiene or for the hydrocyanation of 3-pentenenitrile.

According to the invention, the isomerization is carried out in the presence of a system comprising
a) at least nickel(0)
b) if appropriate, a compound which complexes nickel(0) as a ligand and contains trivalent phosphorus,
c) if appropriate, a Lewis acid.

The preparation of Ni(0)-containing catalyst systems is known per se and, for the purposes of the present invention, may be effected by processes known per se.

In addition, the system additionally comprises a compound suitable as a ligand for nickel(0) which has at least one trivalent phosphorus atom, or a mixture of such compounds. This compound has already been discussed in the present application in the description of the hydrocyanation catalysts.

In addition, the system comprises, if appropriate, a Lewis acid as already described above.

According to the invention, the isomerization provides linear pentenenitrile.

In the context of the present invention, linear pentenenitrile refers to a single such isomer or a mixture of 2, 3, 4 or 5 different such isomers.

The linear pentenenitrile may be cis-2-pentenenitrile, trans-2-pentenenitrile, cis-3-pentenenitrile, trans-3-pentenenitrile, 4-pentenenitrile or mixtures thereof, preferably cis-3-pentenenitrile, trans-3-pentenenitrile, 4-pentenenitrile or mixtures thereof, in particular cis-3-pentenenitrile, trans-3-pentenenitrile or mixtures thereof, which are referred to in the context of the present invention as 3-pentenenitrile, both in each case individually and in a mixture.

The isomerization may be carried out in the presence of a liquid diluent, for example of a hydrocarbon such as hexane, heptane, octane, cyclohexane, methylcyclohexane, benzene, decahydronaphthalene, for example an ether such as diethyl ether, tetrahydrofuran, dioxane, glycol dimethyl ether, anisole, for example an ester such as ethyl acetate, methyl benzoate, or for example a nitrile such as acetonitrile, benzonitrile, or mixtures of such diluents. In a preferred embodiment, isomerization is effected in the absence of such a liquid diluent.

In addition, it has been found to be advantageous to carry out all process steps of the process according to the invention in an nonoxidizing atmosphere, such as under a protective gas atmosphere composed of nitrogen, or a noble gas such as argon.

According to the invention, a mixture comprising 2-methyl-3-butenenitrile and linear pentenenitrile is withdrawn if appropriate from the reaction mixture during the isomerization. The withdrawal may advantageously be distillative.

In a preferred embodiment, a stream comprising 2-methyl-3-butenenitrile and linear pentenenitrile, preferably consisting of 2-methyl-3-butenenitrile and linear pentenenitrile, is withdrawn continuously or quasicontinuously, preferably continuously. It is also possible to continuously or quasicontinuously, preferably continuously, supply the hydrocyanation stream 1 comprising 2-methyl-3-butenenitrile.

In a preferred embodiment, the feed stream may have a content of 2-methyl-3-butenenitrile in the range from 10 to 100% by weight, preferably from 50 to 75% by weight.

In a preferred embodiment, the withdrawn stream may have a content of 2-methyl-3-butenenitrile of from 5 to 80% by weight, preferably from 20 to 60% by weight, and a content of linear pentenenitrile of from 20 to 95% by weight, preferably from 40 to 80% by weight, with the proviso that the sum of the contents of 2-methyl-3-butenenitrile and linear pentenenitrile is at most 100% by weight.

Useful apparatus for the distillation is that which is customary for this purpose, as described, for example, in: Kirk-Othmer, Encyclopedia of Chemical Technology, 3rd Ed., Vol. 7, John Wiley & Sons, New York, 1979, page 870-881, such as sieve tray columns, bubble-cap tray columns, columns having structured packing or columns having random packing.

It is equally possible to withdraw directly from the reactor without separation stages.

The concentration of the stream withdrawn with respect to the molar ratio of 2-methyl-3-butenenitrile to the linear pentenenitrile may be adjusted, depending on the composition of the feed stream, in a technically simple manner by the temperature, the pressure and the reflux ratio in the distillation.

In a first embodiment, the isomerization is effected in an apparatus connection designed therefor, as described, for example, in the German patent application DE with the title "Preparation of linear pentenenitrile" to BASF AG (B03/0436).

In a further embodiment, the isomerization is effected in one or more distillation apparatuses of process step (b).

The temperature in the region of the isomerization zone which is the bottom region in the case of a distillation apparatus as the reaction vessel may be preferably be at least 10° C., more preferably at least 60° C., in particular at least 100° C., especially at least 110°.

The temperature in the region of the isomerization zone which is the bottom region in the case of a distillation apparatus as the reaction vessel may preferably be at most 200° C., more preferably at most 150° C., in particular at most 140° C., especially at most 130° C.

The pressure in the region of the isomerization zone which is the bottom region in the case of a distillation apparatus as the reaction vessel may preferably be at least 5 mbar, more preferably at least 200 mbar, in particular at least 500 mbar, especially at least 600 mbar.

The pressure in the region of the isomerization zone which is the bottom region in the case of a distillation apparatus as the reaction vessel may preferably be at most 5000 mbar, more preferably at most 4000 mbar, in particular at most 3000 mbar.

Equally, the pressure mentioned may be established as the partial pressure of the nitrile stream by introducing an inert gas such as nitrogen or argon (stripping effect).

When a process step (a') is carried out in the process according to the invention, in which 2-methyl-3-butenenitrile is isomerized, a 2-methyl-3-butenenitrile-depleted and a 3-pentenenitrile-enriched isomerization stream 1 is obtained in this isomerization. From this isomerization stream 1, the at least one nickel(0) catalyst is removed to obtain a catalyst stream 1' which comprises the at least one nickel(0) catalyst. In addition, a hydrocyanation stream 2' is obtained which comprises 3-pentenenitrile and 2-methyl-3-butenenitrile.

Preference is given to effecting this separation in the process step (b) present, so that catalyst stream 1' and catalyst stream 1, and also hydrocyanation stream 2' and hydrocyanation stream 2, are identical.

This hydrocyanation stream 2 may if appropriate subsequently be separated in a process step (f) to obtain a 3-pentenenitrile-rich stream 4 and a 2-methyl-3-butenenitrile-rich stream 5.

It is preferred that the 3-pentenenitrile-rich stream 4 which contains preferably at most 1% by weight, more preferably at most 0.5% by weight, in particular at most 0.3% by weight, of 2-methyl-3-butenenitrile is conducted into process step (d). Furthermore, it is preferred that the 2-methyl-3-butenenitrile-rich stream 5 is recycled into process step (a'), where 2-methyl-3-butenenitrile is again isomerized.

It is possible that only a portion of the catalyst stream 2 is used for the hydrocyanation in process step (d) and the remaining portion of the catalyst stream 2 is transferred directly into process step (a') as a bypass stream 1'. In a further embodiment of the process according to the invention, the above-described optional process steps (a') and (f) are therefore run through, in which case, the hydrocyanation stream 1 is conducted directly into process step (b) and the nickel(0) catalyst required for the isomerization in process step (a') is obtained from process step (c) as the bypass stream 1'.

Alternatively, it is also possible that only a portion of the catalyst stream 3 is used for the hydrocyanation in process step (a) and the remaining portion of the catalyst stream 3 is transferred directly into process step (a') as a bypass stream 2'. In a further embodiment of the process according to the invention, the above-described optional process steps (a') and (f) are therefore run through, in which case the hydrocyanation stream 1 is conducted directly into process step (b) and the nickel(0) catalyst required for the isomerization in process step (a') is obtained from process step (e) as the bypass stream 2.

In addition, it is preferred that a fresh or reductively regenerated nickel(0) catalyst is supplied in process step (c) of the process according to the invention.

It is particularly preferred when the process according to the invention is carried out continuously.

The above-described closure of the catalyst circuit results in the nickel(0) loss before the regeneration being preferably between 30 and 80%, more preferably from 30 to 70%, in particular from 40 to 60%, of the original value. This ensures that the catalyst regeneration always forms enough Lewis acid for the hydrocyanation of 3-pentenenitrile, preferably from 0.4 to 8 molar equivalents/nickel, more preferably from 0.4 to 4 molar equivalents/nickel, in particular from 0.4 to 1 molar equivalents/nickel.

The present invention is illustrated in detail with reference to FIGS. 1 to 4.

Figure 1:
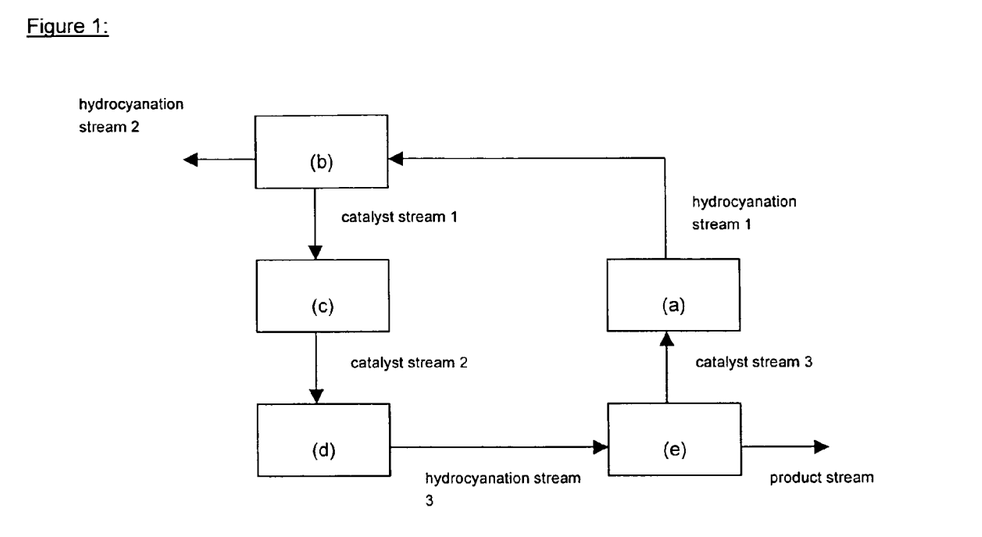

FIG. 1 shows a preferred embodiment of the process according to the invention, in which the hydrocyanation stream I from process step (a) is not subjected to an isomerization.

In process step (a), a hydrocyanation of 1,3-butadiene with hydrogen cyanide initially takes place. From this process step (a) results a hydrocyanation stream 1 which is conducted into process step (b) of catalyst removal. In this process step (b), the at least one nickel(0) catalyst is removed from the hydrocyanation stream 1 to obtain a catalyst stream 1. This catalyst stream 1 comprises the at least one nickel(0) catalyst. In addition, a hydrocyanation stream 2 is obtained in process step (b) and comprises 3-pentenenitrile, 2-pentenenitrile, 2-methyl-2-butenenitrile, 2-methyl-3-butenenitrile and $C_9$ nitriles. The catalyst stream 2 is subsequently transferred into process step (c). Here, the at least one nickel(0) catalyst in the catalyst stream 1 is reductively regenerated. This results in a catalyst stream 2 which is subsequently transferred into the process step of hydrocyanation of 3-pentenenitrile (process step (d)). From this hydrocyanation, a hydrocyanation stream 3 is obtained and is transferred into the catalyst removal of process step (e). This provides a catalyst stream 3 which is recycled into process step (a) of the hydrocyanation of 1,3-butadiene. In addition, a product stream is obtained in process step (e) and comprises adiponitrile.

Figure 2:
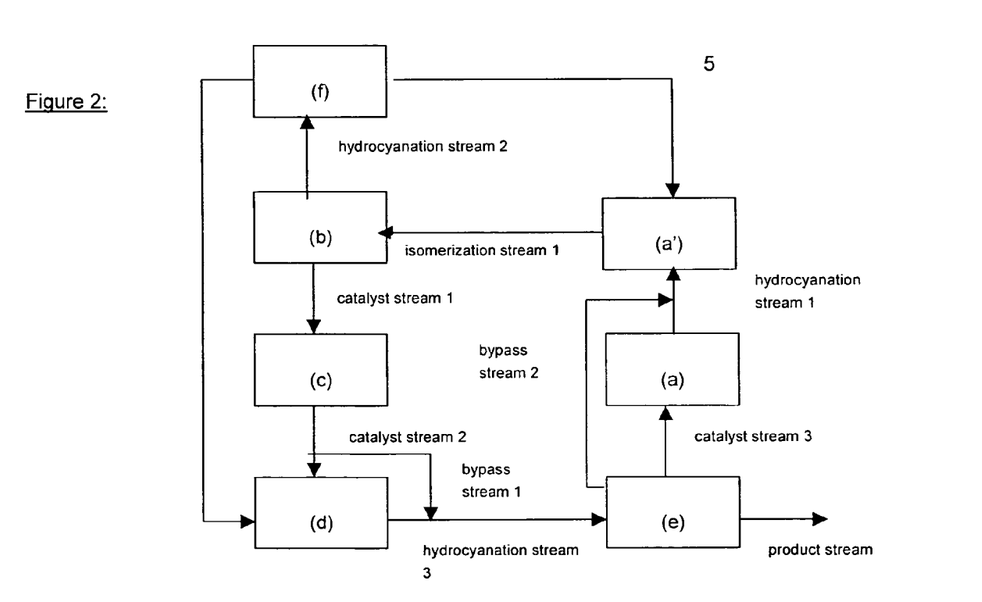

FIG. 2 illustrates one embodiment of the process according to the invention, in which 2-methyl-3-butenenitrile is isomerized to 3-pentenenitrile.

In process step (a), 1,3-butadiene is hydrocyanated over at least one nickel(0) catalyst. This results in a hydrocyanation stream 1 which comprises 3-pentenenitrile, 2-pentenenitrile, 2-methyl-2-butenenitrile, 2-methyl-3-butenenitrile, $C_9$ nitriles, methyl-glutaronitrile and the at least one nickel(0) catalyst. This hydrocyanation stream is subsequently transferred into a process step (a') in which 2-methyl-3-butenenitrile is isomerized to 3-pentenenitrile over at least one nickel(0) catalyst. This provides a 2-methyl-3-butenenitrile-depleted and a 3-pentenenitrile-enriched isomerization stream 1. This isomerization stream 1 is subsequently transferred into process step (b). In this process step (b), the at least one nickel(0) catalyst is removed from the isomerization stream 1 to obtain a catalyst stream 1 which comprises the at least one nickel(0) catalyst. Additionally obtained in this process step is a hydrocyanation stream 2 which comprises 3-pentenenitrile, 2-pentenenitrile, 2-methyl-2-butenenitrile, $C_9$ nitriles and 2-methyl-3-butenenitrile. Subsequently, the catalyst stream 1 is transferred into process step (c) and reductively regenerated. This provides a catalyst stream 2 which is partly transferred into process step (d). The catalyst stream which is not transferred into process step (d) is added as a bypass stream 1 to the hydrocyanation stream 3 resulting from process step (d). In process step (d), 3-pentenenitrile is hydrocyanated over the at least one nickel(0) catalyst in the presence of a Lewis acid which is present in the catalyst stream 2. From process step (d) results a hydrocyanation stream 3 which comprises adiponitrile, the at least one nickel (0) catalyst and the at least one Lewis acid. This hydrocyanation stream is subsequently transferred into process step (e) to remove the at least one nickel(0) catalyst. This removal is effected by extraction with an organic solvent. A catalyst stream 3 is obtained and is partly recycled into process step (a). The portion of the catalyst stream 3 which is not recycled is passed directly into the hydrocyanation stream 1 as a bypass stream 2. In process step (e), a product stream is finally obtained which comprises adiponitrile. Additionally, the hydrocyanation stream 2 obtained in process step (b) is separated in a process step (f) into a 2-methyl-3-butenenitrile-rich stream 5 and a 3-pentenenitrile-rich stream 4. Stream 4 is conducted into process step (d) and stream 5 into process step (a').

Figure 3:
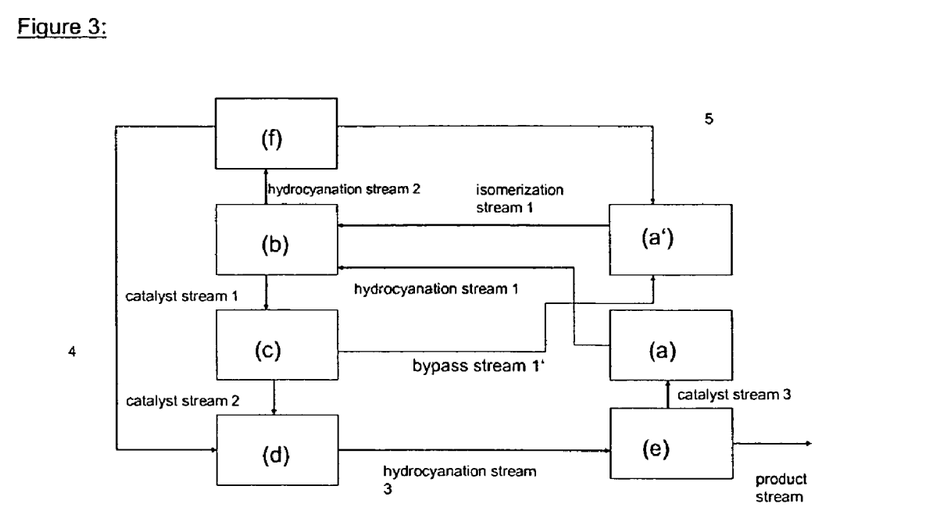

FIG. 3 illustrates one embodiment of the process according to the invention, in which 2-methyl-3-butenenitrile is isomerized to 3-pentenenitrile.

In process step (a), 1,3-butadiene is hydrocyanated over at least one nickel(0) catalyst. This results in a hydrocyanation stream 1 which comprises 3-pentenenitrile, 2-pentenenitrile, 2-methyl-2-butenenitrile, 2-methyl-3-butenenitrile, $C_9$ nitriles, methylglutaronitrile, the at least one nickel(0) catalyst, unconverted 1,3-butadiene and residues of unconverted hydrogen cyanide. This hydrocyanation stream is subsequently transferred into a process step (b). In this process step (b), the at least one nickel(0) catalyst is removed from the hydrocyanation stream 1 to obtain a catalyst stream 1 which comprises the at least one nickel(0) catalyst. In addition, a hydrocyanation stream 2 is obtained in this process and comprises 3-pentenenitrile, 2-pentenenitrile, 2-methyl-2-butenenitrile, $C_9$ nitriles and 2-methyl-3-butenenitrile. This resulting hydrocyanation stream 2 is subsequently separated in a process step (f) into a 2-methyl-3-butenenitrile-rich stream 5 and a 3-pentenenitrile-rich stream 4. Stream 4 is conducted into process step (d) and stream 5 is conducted into an isomerization step (a'). In this process step (a'), an isomerization of 2-methyl-3-butenenitrile to 3-pentenenitrile takes place over at least one nickel(0) catalyst. This provides a 2-methyl-3-butenenitrile-depleted and a 3-pentenenitrile-enriched isomerization stream 1. This isomerization stream 1 is subsequently transferred into process step (b). The nickel(0) catalyst required for the isomerization in process step (a') is obtained from the process step (c) described below as a bypass stream 1'. The catalyst stream obtained in process step (b) is transferred into process step (c) and reductively regenerated. This provides a catalyst stream 2 which is partly transferred into process step (d). The portion of the catalyst stream 2 which is not transferred into process step (d) is added to process step (a') as described above as a bypass stream 1'. In process step (d), 3-pentenenitrile is hydrocyanated over the at least one nickel(0) catalyst in the presence of a Lewis acid which is present in the catalyst stream 2. From process step (d) results a hydrocyanation stream 3 which comprises adiponitrile, the at least one nickel(0) catalyst and the at least one Lewis acid. This hydrocyanation stream 3 is subsequently transferred into process step (e) to remove the at least one nickel(0) catalyst. This removal is effected by extracting with an organic solvent. A catalyst stream 3 is obtained and is recycled into process step (a).

Figure 4:
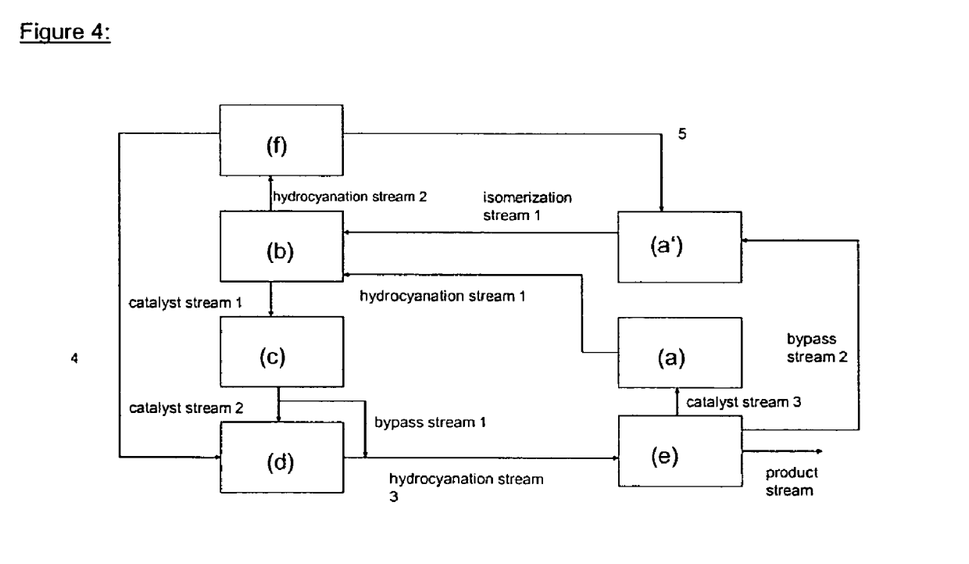

FIG. 4 illustrates one embodiment of the process according to the invention, in which 2-methyl-3-butenenitrile is isomerized to 3-pentenenitrile.

In process step (a), 1,3-butadiene is hydrocyanated over at least one nickel(0) catalyst. This results in a hydrocyanation stream 1 which comprises 3-pentenenitrile, 2-pentenenitrile, 2-methyl-2-butenenitrile, 2-methyl-3-butenenitrile, C$_9$ nitriles, methylglutaronitrile, the at least one nickel(0) catalyst, unconverted 1,3-butadiene and residues of unconverted hydrogen cyanide. This hydrocyanation stream is subsequently transferred into a process step (b). In this process step (b), the at least one nickel(0) catalyst is removed from the hydrocyanation stream 1 to obtain a catalyst stream 1 which comprises the at least one nickel(0) catalyst. In addition, a hydrocyanation stream 2 is obtained in this process and comprises 3-pentenenitrile, 2-pentenenitrile, 2-methyl-2-butenenitrile, C$_9$ nitriles and 2-methyl-3-butenenitrile. This resulting hydrocyanation stream 2 is subsequently separated in a process step (f) into a 2-methyl-3-butenenitrile-rich stream 5 and a 3-pentenenitrile-rich stream 4. Stream 4 is conducted into process step (d) and stream 5 is conducted into an isomerization step (a'). In this process step (a'), an isomerization of 2-methyl-3-butenenitrile to 3-pentenenitrile takes place over at least one nickel(0) catalyst. This provides a 2-methyl-3-butenenitrile-depleted and a 3-pentenenitrile-enriched isomerization stream 1. This isomerization stream 1 is subsequently transferred into process step (b). The nickel(0) catalyst required for the isomerization in process step (a') is obtained from the process step (c) described below as a bypass stream 2. The catalyst stream obtained in process step (b) is transferred into process step (c) and reductively regenerated. This provides a catalyst stream 2 which is partly transferred into process step (d). The catalyst stream which is not transferred into process step (d) is added to the hydrocyanation stream 3 resulting from process step (d) as a bypass stream 1. In process step (d), 3-pentenenitrile is hydrocyanated over the at least one nickel(0) catalyst in the presence of a Lewis acid which is present in the catalyst stream 2. From process step (d) results a hydrocyanation stream 3 which comprises adiponitrile, the at least one nickel(0) catalyst and the at least one Lewis acid. This hydrocyanation stream 3 is subsequently transferred into process step (e) to remove the at least one nickel(0) catalyst. This removal is effected by extraction with an organic solvent. A catalyst stream 3 is obtained and is recycled partly into process step (a). The portion of catalyst stream 3 which has not been recycled is passed directly into process step (a') as a bypass stream 2, as already mentioned.

EXAMPLES

| Abbreviations: | |
|---|---|
| 3PN | linear pentenenitrile isomers (trans-3-, cis-3-, trans-2-, cis-2-, 4-pentenenitrile) |
| C5 waste nitriles | valeronitrile, E- and Z-2-methyl-2-butenenitrile |
| ADN | adiponitrile |
| MGN | sum of 2-methylglutaro- and 2-ethylsuccinonitrile |

| -continued | |
|---|---|
| Abbreviations: | |
| 2M3BN | 2-methyl-3-butenenitrile |
| P | phosphorus |
| Ni(0) | nickel in the 0 oxidation state |
| BD | 1,3-butadiene |
| BU | sum of 1-butene, cis- and trans-2-butene |
| C2BU | cis-2-butene |
| HCN | hydrogen cyanide |
| LL | chelate ligand of the formula 1 |
| NiLL | Ni(0) complex of the chelate ligand LL |
| TBP | tert-butylpyrocatechol |

All data and concentrations are quoted in % by weight.

The concentrations of C5 and C6 nitriles, BD and BU are determined by GC with internal standard (benzonitrile); HCN is quantified by absorption in NaOH and subsequent cyanide titration. Ni(0) is determined by cyclic voltammetry, P by atomic absorption spectroscopy.

Example 1

In example 1, a single catalyst system based on nickel(0) complexes with chelate ligand 1 is used for both hydrocyanations of butadiene to adiponitrile.

1

Ligand 1 (LL) is used in excess compared to Ni(0), so that NiLL and free LL are present. In the second hydrocyanation, ZnCl$_2$ is additionally required. The catalyst cycle over seven process steps is described below.

In a step (1), the following streams are conducted into a loop reactor R1 of capacity 25 l, which is equipped with a nozzle, impulse exchange tube, external pump circulation system and a heat exchanger disposed in the pump circulation system to remove the energy of reaction, and is heated to 367 K:

a) 5.7 kg/h of liquid, unstabilized hydrogen cyanide free of water by distillation (stream 1), b) 15.8 kg/h of a mixture of BD and BU with approx. 90% BD content (stream 6) which is obtained from the recycled stream 5 which is obtained as described in step (2), and added 11.5 kg/h of commercial BD (stream 2), containing 0.25% C2BU, which has been treated by contact with alumina in order to remove water and TBP stabilizer, c) 5.4 kg/h of nickel(0) catalyst solution, obtained as described in this example in step (2), as substream 3 in the bottom of K2.

The stream 4 drawn off from the reactor R1 (27 kg/h) contains a total of 16.2% BD and BU, corresponding to a conversion of 80.4% BD, and also 35.0% 3PN, 29.8% 2M3BN and small amounts of C5 waste nitrile. In addition, the Ni(0) analysis shows 0.4% and the P analysis 1.2%. ADN is present to an extent of 1.0%, additionally 1.0% MGN.

In a step (2), stream 4 is fed to a distillation column K1 which is operated with rectifying and stripping section and is equipped with a falling-film evaporator and divided bottom, and also column internals having structured packing which generate 10 theoretical plates. Column K1 is operated at the top with a direct condenser which consists of a column section provided with structured packing and having a total collecting cup, pumped circulation system and external heat exchanger. The column K1 is operated at an absolute top pressure of 2.0 bar, top temperature 288 K and bottom draw temperature 363 K.

Via the top of column K1, the stream 5 is obtained and is metered together with the fresh BD stream 2 into the reactor R1 as recycle stream 6 as described above. The reflux ratio at the top of column K1 is adjusted such that stream 5 contains approx. 100 ppm of 2M3BN.

Via the top of column K1, 24.9 kg/h of a stream 7 are obtained which contains 3.1% BD, 5.4% BU, 38.0% 3PN and 32.8% 2M3BN, and also additionally the catalyst constituents (analysis: 0.4% Ni(0), 1.3% P). BU is distinctly enriched in relation to BD compared to the feed.

In the bottom of column K1, a stream 9 (2.2 kg/h) is additionally fed in, which is generated in the downstream column K2.

Within the step (2), stream 7 is conducted into a distillation column K2 which is operated in stripping mode and is equipped with falling-film evaporator, top condenser with postcondenser, and column internals with structured packing which generates 10 theoretical plates. The column is operated at an absolute top pressure of 150 mbar, top temperature 329 K and bottom draw temperature 373 K. The vapor stream of the column is partly condensed at 308 K and treated at 263 K with a postcondenser. The BD stream 8 thus depleted of 2M3BN and other pentenenitriles (2.3 kg/h) is compressed in a compressor V1 to an absolute pressure of 1.2 bar (34.3% BD, 59.1% BU, remainder C5 nitriles). The compressed gas stream is condensed at 279 K, for the most part to obtain a stream 9 (see above), and the gas stream 10 (41.5 l (STP)/h, containing 56.2% BU) is disposed of. Stream 9 is recycled in liquid form into the bottom of column K1.

In the column K2, the stream 11 is obtained in a gaseous side draw (24.9 kg/h) and contains approx. 100 ppm of BD, 32.2% 2M3BN and 63.4% 3PN, and also 3.4% C5 waste nitriles. The position of the side draw is selected such that the component 2M3BN is depleted below the side draw in a stripping section in relation to 3PN in the stream 13 obtained via the bottom (approx. 4 theoretical plates below the top). The workup of this stream is described, for example, in DE-A-102 004 004 671 ex. 1 for the stream 11 there.

Into the bottom of column K2 are conducted 21.9 kg/h of the catalyst stream 12 whose preparation is described below in step (7).

In the column K2, the catalyst stream 13 is obtained and contains 2.1% Ni(0), 6.0% P, approx. 100 ppm of 2M3BN and 16.7% 3PN, and additionally approx. 1.0% waste C5 nitriles and 6.8% C6 dinitriles, of which 25% is MGN. The stream 13 is split into substream 3 (5.4 kg/h) which is recycled into reactor R1 as described above. The other portion (stream 14) (14.1 kg/h) is fed to a regeneration in step (3).

In step (3), additional Ni(0) is generated in a Redox reaction in a stirred vessel R3 (50 l, jacketed glass vessel) by feeding 15.7 kg/h of $NiCl_2$ suspension (stream 17; 3.5% by weight in pentenenitrile; circulated by pumping; withdrawn from the pumped circulation line of the reservoir vessel; prepared, for example, as described in example 6 of the application DE-A-103 51 002) and Zn powder is solid form (average particle diameter 11 µm, metering via a Teflon screw from a silo; stream 16; 0.3 kg/h). This Ni(0) is complexed in situ with LL from stream 15 (0.2 kg/h). Additionally formed stoichiometrically in the reaction is a corresponding amount of $ZnCl_2$. The reactor is heated to 80° C. The vessel is blanketed with nitrogen.

In a step (4), the stream 18 leaving step (3) is fed to a loop reactor R3 of capacity 250 l which is equipped with a jet nozzle, impulse exchange tube, external pumped circulation system and heat exchanger to remove heat of reaction. In addition, the following streams are metered in:
a) 10.0 kg/h of liquid, unstabilized hydrogen cyanide freed of water by distillation (stream 20),
b) 56.5 kg/h of pentenenitrile (stream 19) containing 83.3% 3PN and the remainder of C5 waste nitriles.

The stream 21 drawn off from the reactor R3 (96.7 kg/h) contains 36.0% 3PN, and also 39.4% ADN and 2.5% MGN, corresponding to a conversion of 54% pentenenitrile.

In a step (5), stream 23 is fed to a one-stage distillation in a pumping-circulated vessel B2 with external false circulation flash evaporator and a top condenser. The vessel B2 is operated at absolute top pressure 25 mbar, condensation temperature 313 K and bottom draw temperature 343 K.

Via the top of the vessel B2, the stream 22 is obtained (32.5 kg/h) which contains a total of 77.4% 3PN and 21.9% waste C5 nitriles; the remainder is C6 dinitriles. Stream 25 is subsequently worked up as described, for example, in DE-A-102 004 004 683, ex. 2, for the stream 4 there.

Via the bottom of the vessel B2, 64.4 kg/h of a stream 23 having a content of 15.1% 3PN and 3.9% C5 waste nitriles are obtained. The C6 dinitrile content is 59.0% for ADN and 3.6% for MGN. Stream 23 additionally contains the catalyst complex and free ligands (Ni(0) 0.5%, P 1.3%), $ZnCl_2$ (Cl analysis 0.5%), and also, to a small extent, catalyst degradation products.

In a step (6), stream 23 is introduced at the upper end of a countercurrent extraction column K3 and extracted with 96.2 kg/h of a stream 24 containing 92.8% methylcyclohexane as an extractant, and also various pentenenitrile isomers whose preparation is described below. The stream 26 obtained at the top of the extraction consists to an extent of 83.3% of the extractant and contains, in addition to 4.0% 3PN, 0.7% ADN and the catalyst components, nickel(0) complex and free ligands, so that 0.3% Ni(0) and 0.9% P are measured. The zinc chloride remains fully in the bottom draw of the extraction column in stream 25. Stream 25 is subsequently worked up, as described, for example, in DE-A-102 004 004 683, ex. 2, for the stream 7 there, in order to recover unconverted pentenenitrile and MCH present, and to isolate the pure ADN product.

In a step (7), stream 26 is conducted into a distillation column K4 which is equipped with falling-film evaporator, a divided bottom and top condenser, and also column internals having structured packing which generate 12 theoretical plates. The column is operated at absolute top pressure 100 mbar, top temperature 308 K and bottom draw temperature 353 K. In the bottom, pentenenitrile (11.7 kg/h; stream 30) is fed in which has been prepared in exactly the same way as the pentenenitrile in stream 19. In addition, the MCH from the workup of stream 25 is recycled (9.6 kg/h, 88.8% MCH, 9.5% 3PN, remainder waste C5 nitrites) and fed into column K4 as stream 29.

Via the top of column K4, the extractant is recovered and is recycled into extraction column K3 as stream 26 together with a small makeup stream 28 of pure MCH dried to a water concentration below 10 ppm.

At the bottom of column K4, the extracted catalyst is obtained in stream 12 as a solution in pentenenitrile (21.9 kg/h), whose feeding into K2 in step (2) has already been described. This stream contains 43.9% 3PN, 3.5% C5 waste nitrites, 3.3% ADN and 0.3% MGN. The Ni(0) content is determined to be 1.4% and the P content to be 3.9%. The MCH content in stream 12 is adjusted in column K4 to 10 ppm by weight.

What is claimed is:

1. A process for preparing adiponitrile comprising the steps of
   (a) hydrocyanating 1,3-butadiene over at least one nickel (0) catalyst, resulting in a hydrocyanation stream 1 which comprises 3-pentenenitrile, 2-pentenenitrile, 2-methyl-2-butenenitrile, $C_9$ nitriles, 2-methyl-3-butenenitrile, methyiglutaronitrile, the at least one nickel(0) catalyst, unconverted 1,3-butadiene and residues of unconverted hydrogen cyanide,
   (b) removing the at least one nickel(0) catalyst from the hydrocyanation stream 1 to obtain a catalyst stream 1 which comprises the at least one nickel(0) catalyst, and a hydrocyanation stream 2 which comprises 3-pentenenitrile, 2-pentenenitrile, 2-methyl-2-butenenitrile, $C_9$ nitriles and 2-methyl-3-butenenitrile,
   (c) regenerating the at least one nickel(0) catalyst in the catalyst stream 1 by reductive nickel catalyst synthesis with addition of fresh ligand to obtain a catalyst stream 2,
   (d) hydrocyanating 3-pentenenitrile over at least one nickel (0) catalyst and in the presence of at least one Lewis acid, the nickel(0) catalyst and the Lewis acid from at least partly from catalyst stream 2, resulting in a hydrocyanation stream 3 which comprises the at least one nickel(0) catalyst, adiponitrile and the at least one Lewis acid,
   (e) removing the at least one nickel(0) catalyst from the hydrocyanation stream 3 by extraction with an organic solvent to obtain a catalyst stream 3 which comprises the at least one nickel(0) catalyst, and a product stream which comprises adiponitrile, and the catalyst stream 3 can be recycled at least partly into process step (a).

2. A process for preparing adiponitrile comprising the following process steps:
   (a) hydrocyanating 1,3-butadiene over at least one nickel (0) catalyst, resulting in a hydrocyanation stream 1 which comprises 3-pentenenitrile, 2-pentenenitrile, 2-methyl-2-butenenitrile, $C_9$ nitriles, methylglutaronitrile, 2-methyl-3-butenenitrile, the at least one nickel(0) catalyst, unconverted 1,3-butadiene and residues of unconverted hydrogen cyanide,
   (a') isomerizing 2-methyl-3-butenenitrile which is present in the hydrocyanation stream 1 to 3-pentenenitrile over at least one nickel(0) catalyst to obtain a 2-methyl-3-butenenitrile-depleted and a 3-pentenenitrile-enriched isomerization stream 1,
   (b) removing the at least one nickel(0) catalyst from the isomerization stream 1 to obtain a catalyst system 1 which comprises the at least one nickel(0) catalyst, and a hydrocyanation stream 2 which comprises 3-pentenenitrile, 2-pentenenitrile, 2-methyl-2-butenenitrile, $C_9$ nitriles and 2-methyl-3-butenenitrile,
   (c) regenerating the at least one nickel(0) catalyst in the catalyst stream 1 by reductive nickel catalyst synthesis with addition of fresh ligand to obtain a catalyst stream 2,
   (d) hydrocyanating 3-pentenenitrile over at least one nickel (0) catalyst and in the presence of at least one Lewis acid, the nickel(0) catalyst and the Lewis acid stemming at least partly from catalyst stream 2, resulting in a hydrocyanation stream 3 which comprises adiponitrile, the at least one nickel(0) catalyst and the at least one Lewis acid,
   (e) removing the at least one nickel(0) catalyst from the hydrocyanation stream 2 by extraction with an organic solvent to obtain a catalyst stream 3 which comprises the at least one nickel(0) catalyst, and a product stream which comprises adiponitrile, and the catalyst stream 3 can be recycled at least partly into process step (a).

3. The process according to claim 2, further comprising process step (f), in which the hydrocyanation stream 2 is separated and a 3-pentenenitrile-rich stream 4 and a 2-methyl-3-butenenitrile-rich stream 5 are obtained.

4. The process according to claim 3, wherein the 3-pentenenitrile-rich stream 4 is directed into process step (d).

5. The process according to claim 3, wherein the 2-methyl-3-butenenitrile-rich stream 5 is directed into process step (a').

6. The process according to claim 1, wherein the process sequence begins with process step (d) in the first run so that fresh Lewis acid and fresh nickel(0) catalyst and/or reductively regenerated nickel(0) catalyst are used.

7. The process according to claim 1, wherein 3-pentenenitrile hydrocyanated in process step (d) stems comes from the hydrocyanation stream 1.

8. The process according to claim 1, wherein only a portion of the catalyst stream 2 is used for the hydrocyanation in process step (d) and the remaining portion of the catalyst stream 2 is transferred directly into process step (e).

9. The process according to claim 2, wherein only a portion of the catalyst stream 2 is used for the hydrocyanation in process step (d) and the remaining portion of the catalyst stream 2 is transferred directly into process step (a').

10. The process according to claim 2, wherein only a portion of the catalyst stream 3 is used for the hydrocyanation in process step (a) and the remaining portion of the catalyst stream 3 is transferred directly into process step (a').

11. The process according to claim 1, wherein a fresh and/or reductively regenerated nickel(0) catalyst is fed into process step (c).

12. The process according to claim 1, which is carried out continuously.

13. The process according to claim 2, wherein the process sequence begins with process step (d) in the first run so that fresh Lewis acid and fresh nickel(0) catalyst and/or reductively regenerated nickel (0) catalyst are used.

14. The process according to claim 2, wherein 3-pentenenitrile hydrocyanated in process step (d) comes from the hydrocyanation stream 1 and isomerization stream 1.

15. The process according to claim 2, wherein only a portion of the catalyst stream 2 is used for the hydrocyanation in process step (d) and the remaining portion of the catalyst stream 2 is transferred directly into process step (e).

16. The process according to claim 3, wherein only a portion of the catalyst stream 2 is used for the hydrocyanation in process step (d) and the remaining portion of the catalyst stream 2 is transferred directly into process step (e).

* * * * *